US012661449B2

(12) United States Patent
Wang et al.

(10) Patent No.: US 12,661,449 B2
(45) Date of Patent: Jun. 23, 2026

(54) POWER PACK ASSEMBLY

(71) Applicant: SHL MEDICAL AG, Zug (CH)

(72) Inventors: Hsuan Wang, Taoyuan City (TW);
Jared Schwartzentruber, New York,
NY (US)

(73) Assignee: SHL Medical AG, Zug (CH)

( * ) Notice: Subject to any disclaimer, the term of this
patent is extended or adjusted under 35
U.S.C. 154(b) by 937 days.

(21) Appl. No.: 17/634,641

(22) PCT Filed: Sep. 7, 2020

(86) PCT No.: PCT/EP2020/074908
§ 371 (c)(1),
(2) Date: Feb. 11, 2022

(87) PCT Pub. No.: WO2021/058269
PCT Pub. Date: Apr. 1, 2021

(65) Prior Publication Data
US 2022/0280723 A1 Sep. 8, 2022

Related U.S. Application Data

(60) Provisional application No. 62/903,951, filed on Sep.
23, 2019.

(30) Foreign Application Priority Data

Oct. 15, 2019 (EP) ..................................... 19203150

(51) Int. Cl.
*A61M 5/20* (2006.01)
*A61M 5/32* (2006.01)
*A61M 5/46* (2006.01)

(52) U.S. Cl.
CPC ......... *A61M 5/20* (2013.01); *A61M 2005/206*
(2013.01); *A61M 5/326* (2013.01); *A61M 5/46*
(2013.01)

(58) Field of Classification Search
CPC .......... A61M 5/20; A61M 5/326; A61M 5/46;
A61M 2005/206
See application file for complete search history.

(56) References Cited

U.S. PATENT DOCUMENTS

| | | | |
|---|---|---|---|
| 2011/0301534 A1* | 12/2011 | Renz ................... | A61M 5/2066 |
| | | | 604/82 |
| 2012/0056019 A1 | 3/2012 | Renz et al. | |
| 2019/0038837 A1* | 2/2019 | Bokelman ......... | A61M 5/31513 |

FOREIGN PATENT DOCUMENTS

WO 2014/008393 A1 1/2014

OTHER PUBLICATIONS

International Search Report and Written Opinion for Int. App. No.
PCT/EP2020/074908, mailed Oct. 12, 2020.

* cited by examiner

*Primary Examiner* — Chelsea E Stinson
*Assistant Examiner* — Nelson Louis Alvarado, Jr.
(74) *Attorney, Agent, or Firm* — McDonnell Boehnen
Hulbert & Berghoff LLP

(57) ABSTRACT

A power pack assembly for a medicament delivery device is
presented having a housing extending along a longitudinal
axis and having a proximal and a distal end, a container
carrier unit arranged longitudinally and bi-directionally
movable in relation to the housing, a plunger pusher releas-
ably connected to the container carrier unit, and an actuator
unit connected to the plunger pusher, wherein the actuator
unit is configured to drive the plunger pusher in a sequence
in which the plunger pusher and the container unit are
moved together distally relative to the housing until a virtual
distal stop is met. Proximal movement of the plunger pusher
causes the container carrier unit to interact with a proximal
stop element of the housing whereby the plunger pusher is (Continued)

released from the container carrier unit and the plunger pusher continues to move proximally a further distance.

20 Claims, 10 Drawing Sheets

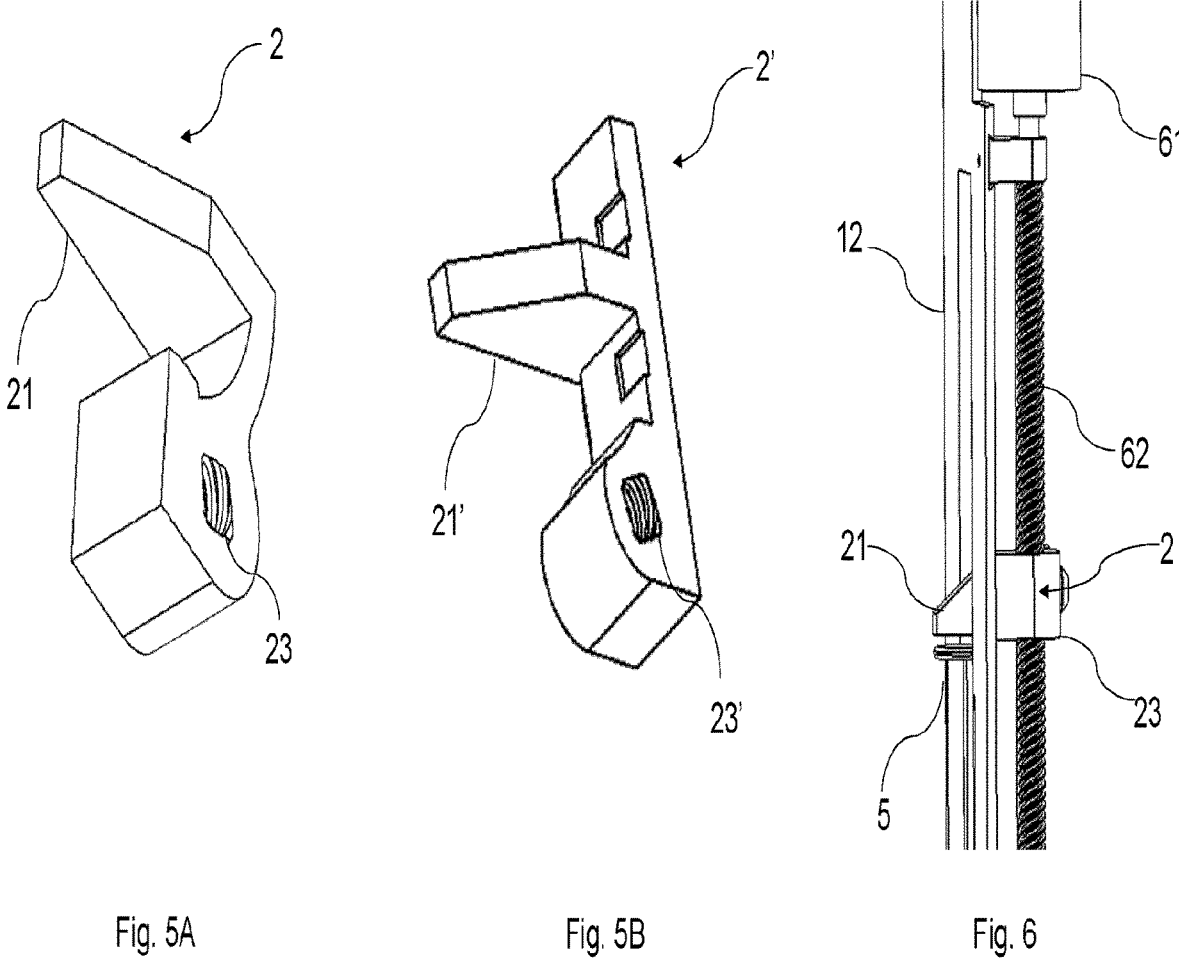
Fig. 5A                    Fig. 5B                    Fig. 6

35a     35     22a

3

35  21

POWER PACK ASSEMBLY

CROSS REFERENCE TO RELATED APPLICATIONS

The present application is a U.S. National Phase Application pursuant to 35 U.S.C. § 371 of International Application No. PCT/EP2020/074908 filed Sep. 7, 2020, which claims priority to U.S. Provisional Patent Application No. 62/903,951, filed Sep. 23, 2019, and European Patent Application No. 19203150.8 filed Oct. 15, 2019. The entire disclosure contents of these applications are herewith incorporated by reference into the present application.

TECHNICAL FIELD

The present disclosure relates to a power pack assembly for a medicament delivery device and more particularly for an automatic medicament delivery device.

BACKGROUND

Medicament delivery devices such as auto-injectors, inhalers, and on-body devices are generally known for the self-administration of a medicament by patients without formal medical training. As just one example, patients suffering from diabetes may require repeated injections of insulin. Other patients may require regular injections of other types of medicaments, such as a growth hormone. Reusable auto-injectors are commonly used by patients who are required to take repeated injections.

Since medicament delivery devices are designed for patients without formal medical training and operation of those medicament delivery devices might be taking place in a patient's own house which is usually not in a place of professional health/medical care, e.g. hospital, clinic or health centres, there is a demand for simplifying the manipulation step of medicament delivery devices and many medicament delivery devices on the market are therefore having a number of automatic or semi-automatic features in order to facilitate the use for a user, in particular when used for self-administration.

WO2014/008393A1 discloses a motor driven medicament delivery device with a coupling mechanism between a cartridge carrier and a plunger carrier, and is configured to couple the movement between the cartridge carrier and the plunger carrier. The coupling mechanism through a transfer instrument, which is formed of a rubbery material, and is an independent separate element in relation to both the cartridge carrier and the plunger carrier. The coupling mechanism is performed by the selective engagement with the transfer instrument and the cartridge carrier and/or the plunger carrier.

However, the rubber transfer instrument might be damaged or loose after long time use, so there is a risk that the transfer instrument might be stuck between the cartridge carrier and the plunger carrier, and causes the damage of the medicament delivery device. Further, using an extra element to couple the cartridge carrier and the plunger carrier requires a precise calculation of tolerances of all involved elements, otherwise the transfer instrument might become stuck at the beginning, or it might be compressed between the cartridge carrier and the plunger carrier such that the coupling mechanism cannot perform properly. For example, the cartridge carrier and the plunger carrier might move together, but since the transfer instrument is compressed, the cartridge carrier and the plunger carrier may instead move in relation to one another.

SUMMARY

An object of the present disclosure is to provide a more robust and reliable power pack assembly, and more specifically, for a reusable medicament delivery device or a training device of the medicament delivery device, which avoids the problems of the prior art.

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial", refer to a direction extending from the proximal end to the distal end and along the device or components thereof in the direction of the longest extension of the device and/or component.

Similarly, the terms "traverse", "transversal", "transversally" refer to a direction generally perpendicular to the longitudinal direction.

An object of this disclosure is to provide a simple and reliable way of operating a reusable medicament delivery device with a driving force element as e.g. a single driven motor associated with a more simple and reliable coupling mechanism for coupling a medicament container and a plunger pusher in a motor driven medicament delivery device.

According to an aspect of the disclosure, the object is achieved by a robust and reliable power pack assembly according to claim 1.

There is provided a power pack assembly for a medicament delivery device comprising: a housing base extending along a longitudinal axis and having a proximal and a distal end; a container carrier unit arranged longitudinally and bi-directionally movable in relation to the housing base; a plunger pusher releasably connected to the container carrier unit; an actuator unit connected to the plunger pusher; wherein the actuator unit is configured to drive the plunger pusher in a sequence in which the plunger pusher and the container unit are together distally moved in relation to the housing base until a virtual distal stop is met; followed by a proximal movement until the container carrier unit interacts with a proximal stop element of the housing whereby the plunger pusher is released from the container carrier unit; and the plunger pusher continues to move proximally a further distance.

According to another aspect of the disclosure, the plunger pusher is releasably connected to the container carrier unit by a coupling element; wherein the coupling element is fixedly connected or integrally to the container carrier unit.

According to one embodiment, the coupling element comprises a flexible member of the container carrier unit.

According to one embodiment, the coupling element comprises a guide slot.

According to one embodiment, the coupling element comprises a holding ledge.

According to one embodiment, the housing base comprises a track which is configured to force the flexible member to be in contact with the plunger pusher until the container carrier unit interacts with the proximal stop element of the housing base such that the flexible member is allowed to flex and thereby release the plunger pusher from the container carrier unit.

According to one embodiment, the track comprises a recess.

According to one embodiment, the flexible member comprises a ledge, which abuts with the plunger pusher.

According to one embodiment, the power pack assembly further comprises a resilient member arranged between the housing base and the container carrier unit; for exerting a force on the container carrier unit.

According to one embodiment, the actuator unit is configured to regulate the exerted force of the resilient member on the container carrier unit.

According to one embodiment, the actuator unit comprises a driving force element, a gearbox, and a lead screw, wherein a first end of the lead screw is connected to the driving force element through the gearbox; and a second end of the lead screw is connected to the plunger pusher.

According to one embodiment, the driving force element is a motor.

According to one embodiment, the plunger pusher further comprises a rod element.

According to one embodiment, the power pack assembly further comprises an electronics set, which comprises a primary detector and a controller configured to control the motor.

According to one embodiment, the primary detector is configured to detect a position of the plunger pusher in relation to the housing base.

According to one embodiment, the primary detector is configured to detect a contact of the plunger pusher and a portion of the housing base.

According to one embodiment, the primary detector can be an optical sensor, e.g. an infra-red emitter and receiver; a magnetic sensor or encoder, a capacitance sensor, a impedance sensor, a mechanical switch, a pressure sensor, a force resistor or any other suitable sensor using for detecting the position of an object or a contact of an object.

According to one embodiment, the virtual distal stop is a programmable stop condition in the controller; such that the distal movement of the plunger pusher and the container carrier unit is stopped upon a stop event which is detected by the primary detector.

According to one embodiment, the programmable stop condition in the controller is met once the stop event is detected; so that the actuator unit is stopped by the controller.

According to one embodiment, power pack assembly is included in a medicament delivery device.

According to one embodiment, the medicament delivery device can be an injection device, an infusion device, an on-body device, in inhalation device or a medical sprayer.

According to one embodiment, the medicament delivery device further comprises a secondary sensor configured to detect an event of the medicament delivery device; wherein the event acts as the stop condition of the controller.

According to one embodiment, the programmable stop condition in the controller is met once the stop event is detected by the secondary detector; so that the actuator unit is stopped by the controller.

According to one embodiment, the secondary detector can be the same or different type of sensor as the primary detector.

According to one embodiment, the secondary detector is configured to detect a position of a protective cap of the medicament delivery device.

According to one embodiment, the secondary detector is configured to detect a position of another protective cap of medicament container of the medicament delivery device.

According to one embodiment, the primary detector is configured to detect an exposure of a medicament delivery member.

According to one embodiment, the primary detector is configured to detect a position of a medicament delivery member.

Other aspects, features, and advantages will be apparent from the summary above, as well as from the description that follows, including the figures and the claims.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments will now be described, by way of example, with reference to the accompanying drawings, in which:

FIGS. 5A-5B displays the plunger pusher of different embodiments and in detail.

FIG. 6 displays the connection between the plunger pusher and the actuation unit.

DETAILED DESCRIPTION

The power pack assembly and the reusable medicament delivery device comprising said power pack assembly will now be described fully hereinafter with reference to the accompanying drawings, in which exemplifying embodiments are shown. The power pack assembly and the reusable medicament delivery device comprising said power pack assembly may, however, be embodied in many different forms and should not be construed as limited to the embodiments set forth herein; rather, these embodiments are provided by way of example so that this disclosure will be thorough and complete, and will fully convey the scope of the power pack assembly and the reusable medicament delivery device comprising said power pack assembly to those skilled in the art. Like numbers refer to like elements throughout the description.

Figure 1:
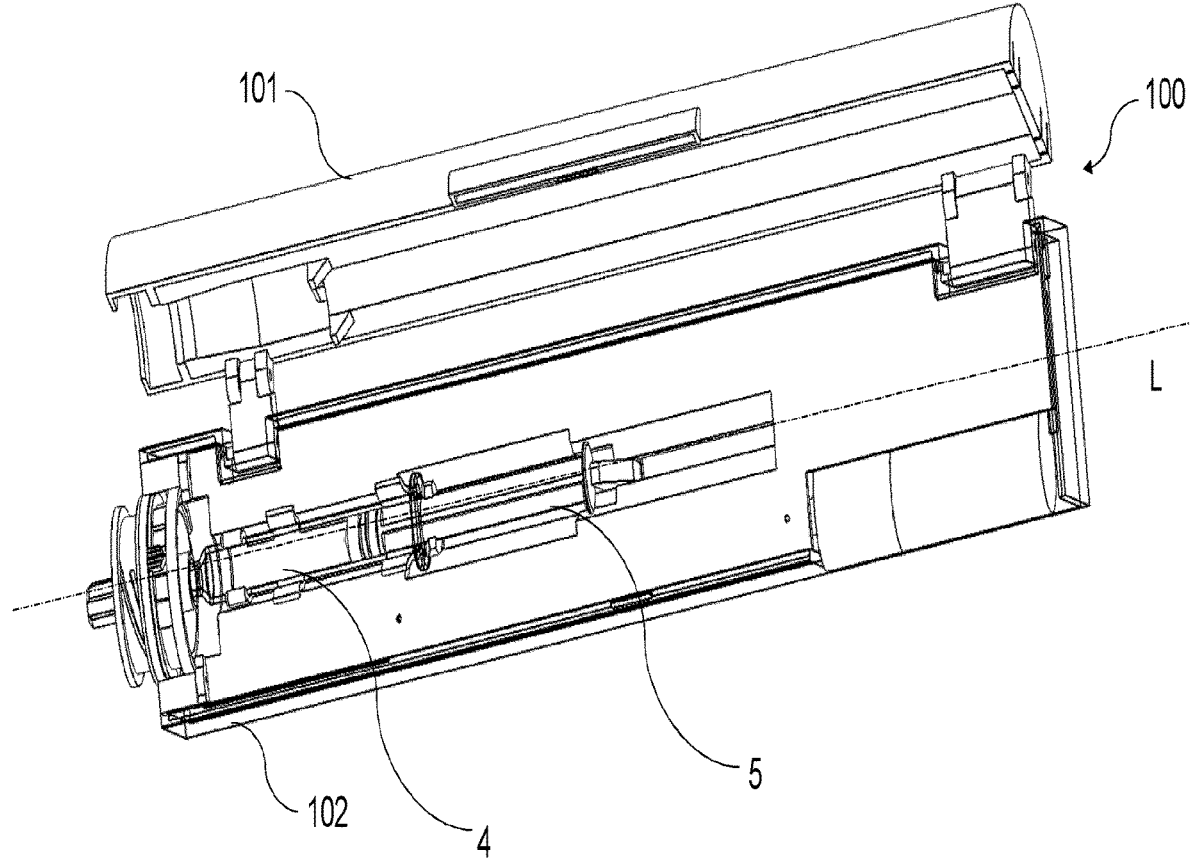
FIG. 1 displays a reusable medicament delivery device having an exchangeable medicament container.
Figures 2A, 2B:
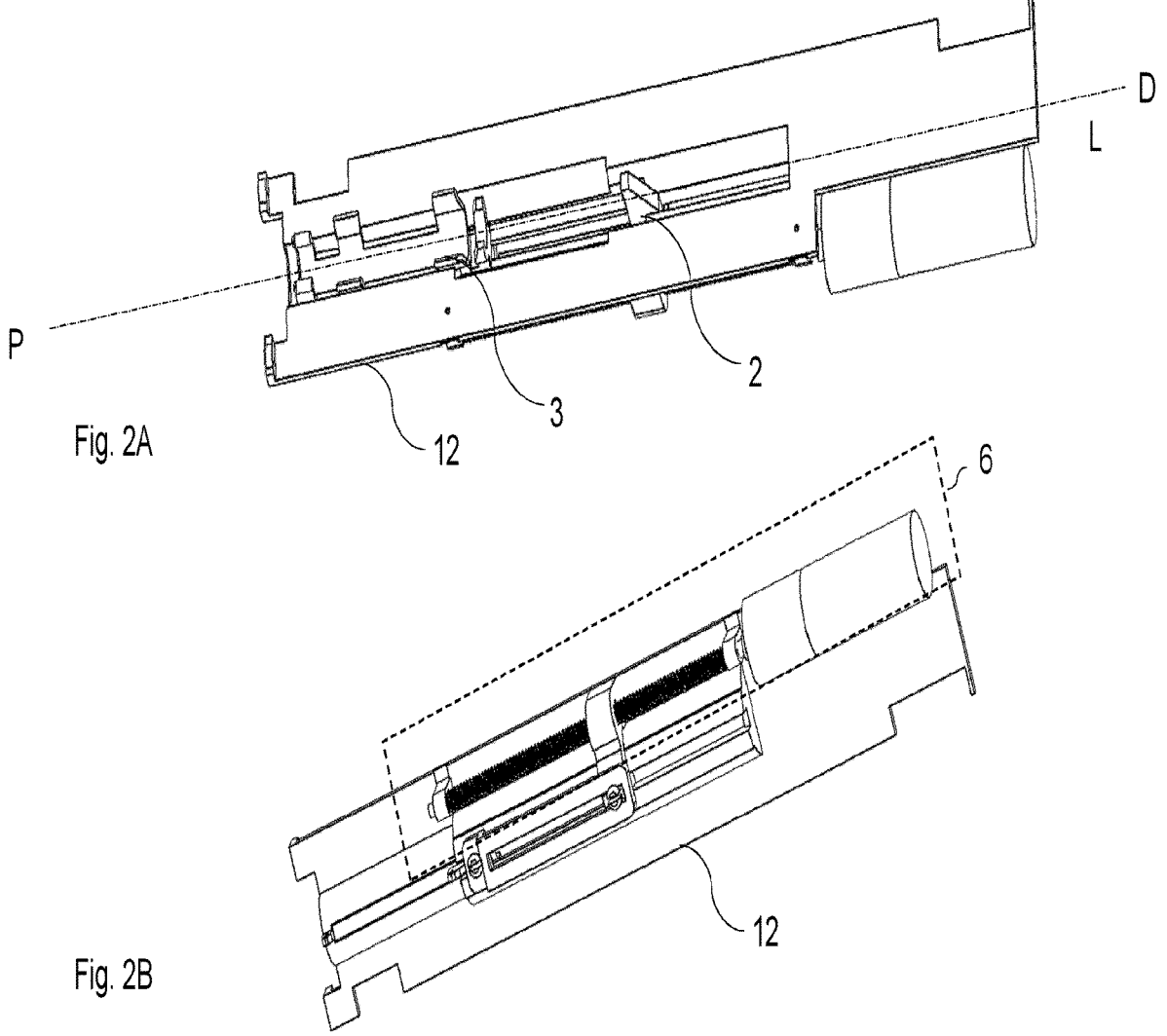
FIGS. 2A-2B displays the power pack assembly.
Figures 3A, 3B:
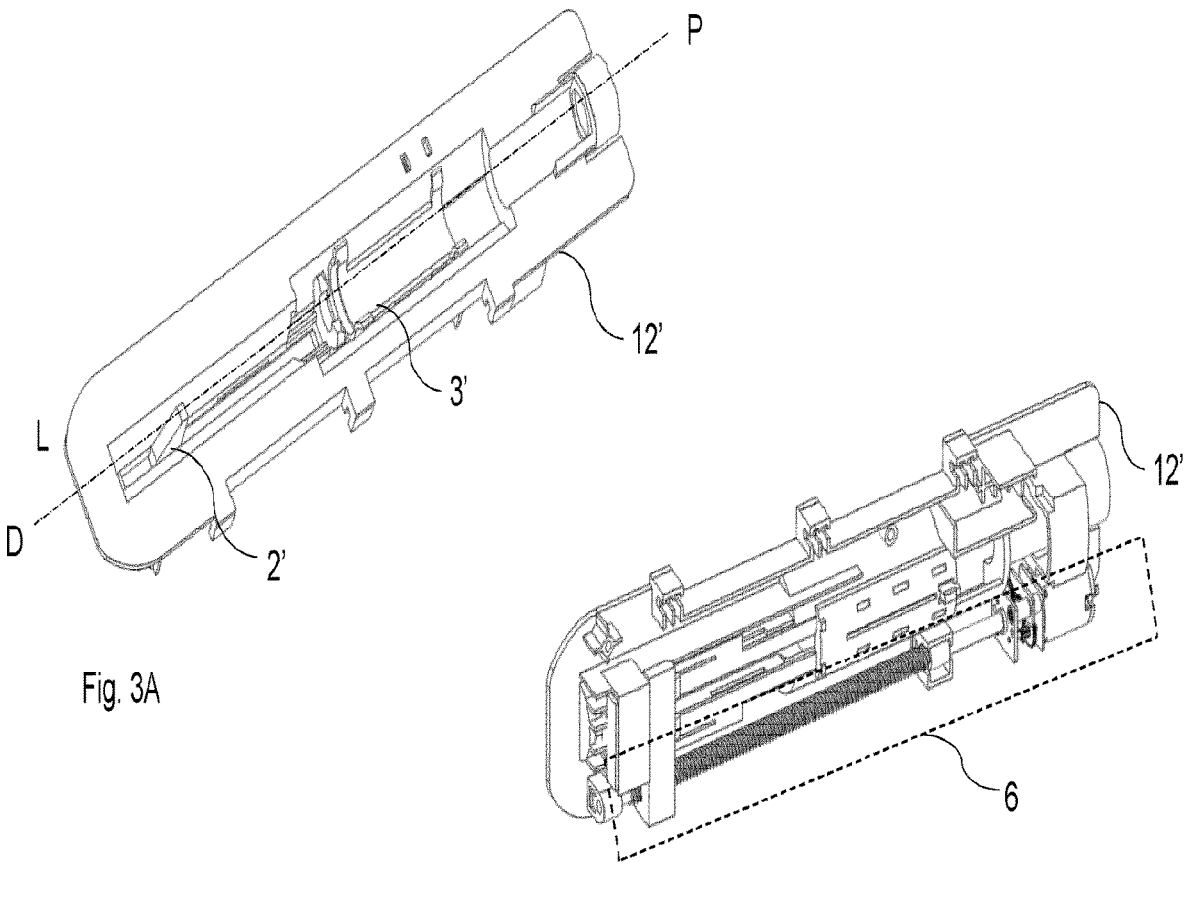
FIGS. 3A-3B displays the power pack assembly in an alternative embodiment.

FIG. 1 illustrates a power pack assembly arranged in a reusable medicament delivery device (100). The reusable medicament delivery device (100) having an exchangeable medicament container (4). The reusable medicament delivery device comprises a housing (100) extending along a longitudinal axis (L) and having a proximal and a distal end. The housing (100) may further comprises a case part (101) and a base part (102). Further, the exchangeable medicament container (4) comprises a plunger rod (5).

FIGS. 2A-2B and 3A-3B illustrate the power pack assembly in two embodiments. The power pack assembly comprises a housing base (12; 12') configured to be associated with the base part (102) of the reusable medicament delivery device (100) and wherein the housing base (12; 12') extends along the longitudinal axis (L) and having a proximal (P) and a distal end (D). The power pack assembly further comprises a container carrier unit (3; 3') arranged longitudinally and bi-directionally movable in relation to the housing base (12; 12'); a plunger pusher (2; 2') axially movable and rotational fixed arranged in relation to the housing base (12; 12'), and an actuator unit (6) associated with the plunger pusher (2; 2'). The container carrier unit (3; 3') is configured to receive the exchangeable medicament container (4) which comprises the plunger rod (5). The plunger pusher (2; 2') is releasably connected to the container carrier unit (3; 3') and is configured to contact the distal end of the plunger rod (5) of the medicament container. In the shown embodiment, the medicament container (4) comprises a barrel configured to contain a medicament; a medicament delivery member arranged on the proximal end of the barrel and configured to act as an outlet of the medicament; a rubber stopper arranged on the distal end of the barrel and configured to seal the distal end of the barrel; the plunger rod (5) arranged on the distal end of the barrel and configured to abut the stopper and actuate the stopper in the proximal direction upon delivering the medicament. In an alternative embodiment (not shown), the plunger rod is arranged on the plunger pusher (2; 2'), so that the exchangeable medicament container may only comprises the stopper to seal the distal end of the barrel. In another alternative embodiment, a user may mount the medicament delivery member to the proximal end of the exchangeable medicament container (4), so that the exchangeable medicament container (4) may only comprises a sealing membrane on the proximal end of the barrel instead the medicament delivery member.

Figure 4A:
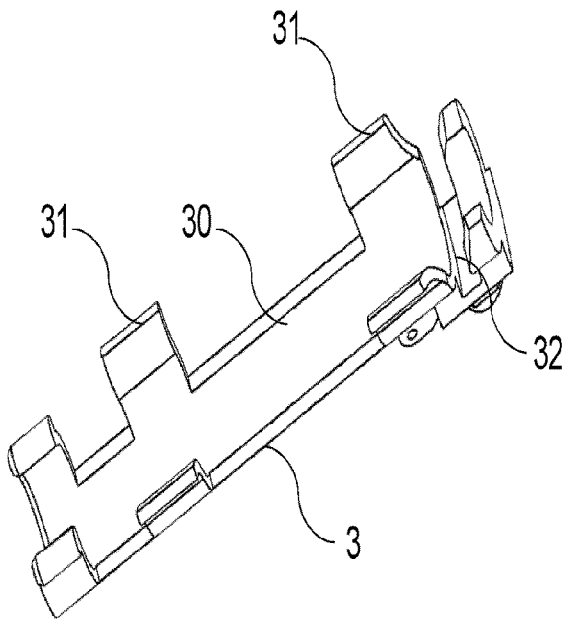
FIGS. 4A-4B displays the container carrier unit in detail.
Figure 4B:

FIGS. 4A-4B illustrate the container carrier unit (3) in detail. The container carrier unit (3) comprises a receiving portion (30) configured to receive the medicament container (4), the receiving portion may be a recess or a sleeve; a gripping portion (31), configured to grip the barrel of the medicament container (4) so that the medicament container (4) can be fixedly arranged in the container carrier unit (3) and/or compensate the tolerance of the diameter of the barrel of the medicament container. The gripping portion (31) may be arranged adjacent to the receiving portion (30) as shown in FIG. 4A, or may be arranged on the inner surface or as an independent element arranged inside the receiving portion (30). The gripping portion may be a part of gripping arms as shown in FIG. 4A, or a C-shape clip or a ring shape element. The container carrier unit (3) may further comprises a retaining portion (32) configured to receive a flange of the medicament container (4), if it comprises a flange, and support the flange so that the medicament container cannot axially move in relation of the container carrier unit (3). The retaining portion (32) may be a recess or a ledge and may further comprise a resilient part to absorb a shock on the flange of the medicament container; or to accommodate wider thickness tolerances of the flange (41) of the medicament container, which is usually corresponding to the size of the medicament container. So that the container carrier unit (3) is compatible with different size of medicament containers. The container carrier unit (3) may further comprises a connecting portion (34) as shown in FIG. 4B.

FIGS. 5A-5B illustrate two embodiments of the plunger pusher (2; 2') in detail. The plunger pusher (2; 2') comprises a pushing portion (21) configured to actuate on the plunger rod (5) or on the stopper of the medicament container (4). In the embodiment shown in FIG. 5A-5B, the pushing part (21; 21') is configured to abut or directly contact the plunger rod (5) of the medicament container (4) as shown in FIG. 6; however, in another embodiment the medicament container (4) does not comprise the plunger rod; the pushing portion (21; 21') will then be modified by including a rod element which is configured to abut or directly contact the stopper of the medicament container (4). The plunger pusher (2; 2') further comprises a transition portion (23; 23').

FIG. 6 illustrates parts of the actuator unit (6) which comprise a main portion (61), and a lead rod (62) associated with the transition portion (23; 23') of the plunger pusher. In some embodiments, the actuator unit may comprise a gearbox. The main portion (61) is configured to act as a driving force element for moving the lead rod (62). In the shown embodiments, the lead rod (62) is a lead screw associated with the transition portion (23; 23') of the plunger pusher through a threaded connection and the main portion (61) is a motor (803) which is associated with the lead screw either directly or through a gearbox. In an alternative embodiment, the gearbox can be replaced by a gear or a cogwheel; such as the lead rod (62) is fixedly arranged on the central portion of the gear and the motor is connected to teeth arranged on the peripheral portion of the gear. The motor is fixedly connected to the housing base (12). In a preferred embodiment, the lead screw (62) is parallel arranged in relation to the medicament container (4) and fixedly supported by supporting elements, which are fixedly connected to the housing base (12). The pushing portion (21; 21') of the plunger pusher (2; 2') is transversally arranged through the housing base (12) for connecting to the plunger rod (5). In the shown embodiments, the output from the motor is configured to set the lead screw (62) in rotation without axial movement. Since the plunger pusher (2; 2') is rotationally fixed in relation to the housing base (12), the rotation of the lead screw (62) will convert into the axial movement of the plunger pusher (2; 2').

Figure 7A:
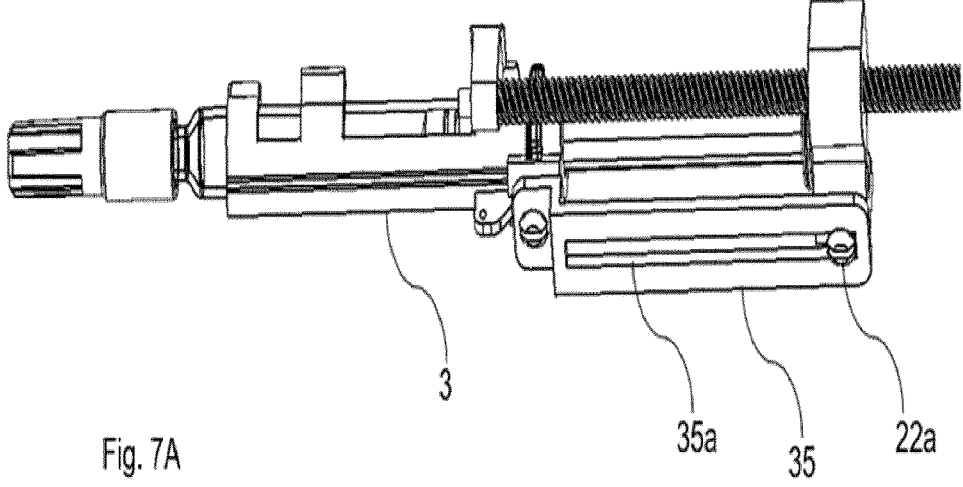
FIGS. 7A-7B displays the coupling element of different embodiments.
Figure 7B:
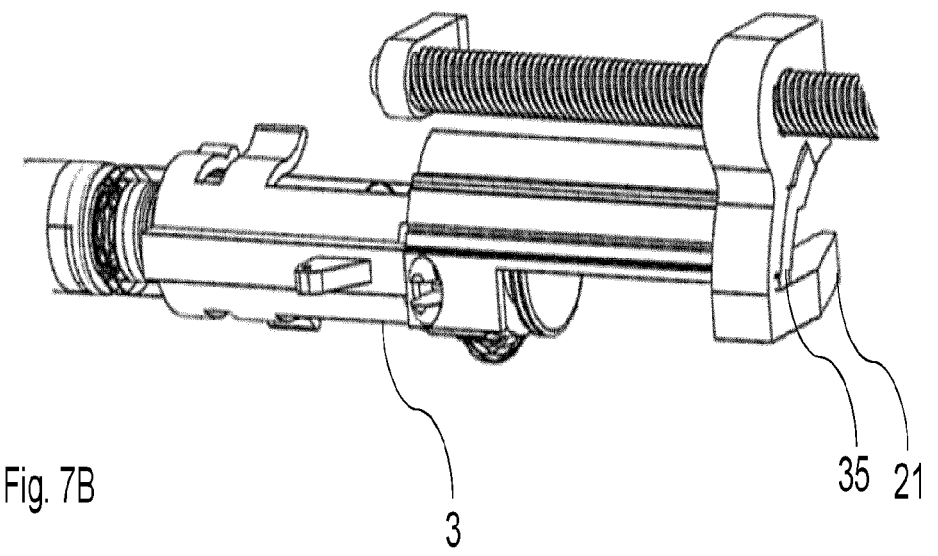

FIGS. 7A-7B illustrate different embodiments of a coupling mechanism between the container carrier unit (3) and the plunger pusher (2) in the first embodiment. The plunger pusher (2) is releasably and reversibly connected to the container carrier unit (3) by a coupling element (35). So when the plunger pusher (2) is connected to the container carrier unit (3), the plunger pusher (2) and the container carrier unit (3) are configured to move axially together. When the plunger pusher (2) is released from the container carrier unit (3), the plunger pusher (2) is configured to axially move in relation to the container carrier unit (3). The coupling element (35) is fixedly connected or integrally to the container carrier unit (3). The container carrier unit (3) is configured to be pulled towards the proximal end by a biased element, preferably, a resilient member (7). The arrangement of the resilient member (7) will be explained in detail below.

In one embodiment as shown in FIG. 7A, the coupling element (35) comprises a guide slot (35a) configured to guide the movement of a connection piece (22a) integral or arranged to the plunger pusher (2). The connection piece (22a) is configured to abut the distal end of the guide slot (35a) when the plunger pusher (2) and the container carrier unit (3) are connected together, so that the plunger pusher (2) and the container carrier unit (3) are moved distally and axially together. Further, since the container carrier unit (3) is pulled towards the proximal end, the pulling force will thereby keep the connection piece (22a) and the distal end of the guide slot (35a) abutting each other. When the plunger pusher (2) moves towards the proximal end together with the connection piece (22a), the pulling force will also pull the container carrier unit (3) towards the proximal end until the container carrier unit (3) is completely stopped by a mechanical stop interface or until the resilient member (7) reaches its relax configuration, namely no more energy is stored in the resilient member (7). The connection piece (22a) will thereby be able to move along the guide slot (35a) towards the proximal end together with the plunger pusher (2), so that the plunger pusher (2) is able to move axially in relation to the container carrier unit (2).

In an alternative embodiment as shown in FIG. 7B, the coupling element (35) is a holding ledge (35), configured to engage on a edge of the plunger pusher (2). The holding ledge (35) can be a part arranged on the container carrier unit (3) or on a part of an independent component which is axially fixed to the container carrier (3). As described above, the container carrier unit (3) is pulled towards the proximal end by the resilient member (7). When the holding ledge engages with the plunger pusher (2), the plunger pusher (2) and the container carrier unit (3) are connected and configured to axially and distally move together. Since the container carrier unit (3) is pulled towards the proximal end, the pulling force will thereby keep the plunger pusher (2) and the coupling element (35) to be in contact. When the plunger pusher (2) moves towards the proximal end, the pulling force will also pull the container carrier unit (3) towards the proximal end. Therefore, when the plunger pusher (2) is moving proximally, it will always be in contact with the coupling element (35) until the container carrier unit (3) is completely stopped by a mechanical stop interface or until the resilient member (7) is in its relax configuration, namely no more energy is stored in the resilient member (7). The plunger pusher (2) will thereby be able to no longer have contact with the coupling element (35) and continue with the proximal movement, so that the plunger pusher (2) is able to move axially in relation to the container carrier unit (2).

Figure 8A:
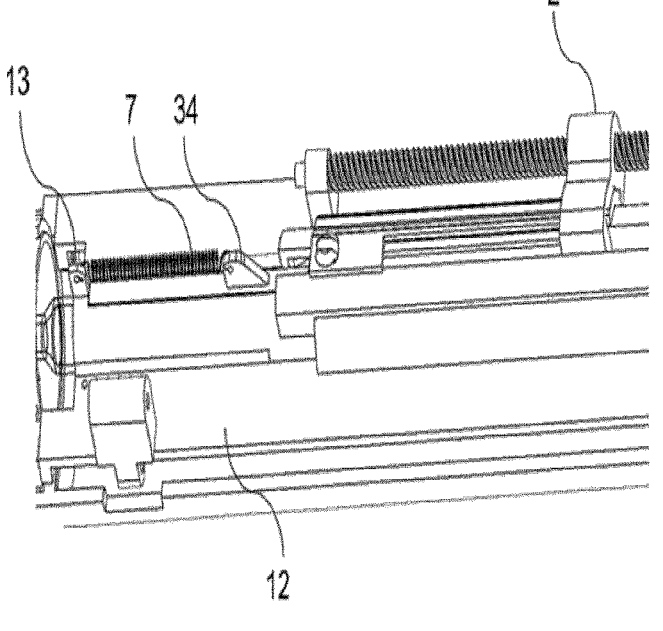
FIGS. 8A-8B displays the resilient member arranged in the power pack assembly.
Figure 8B:
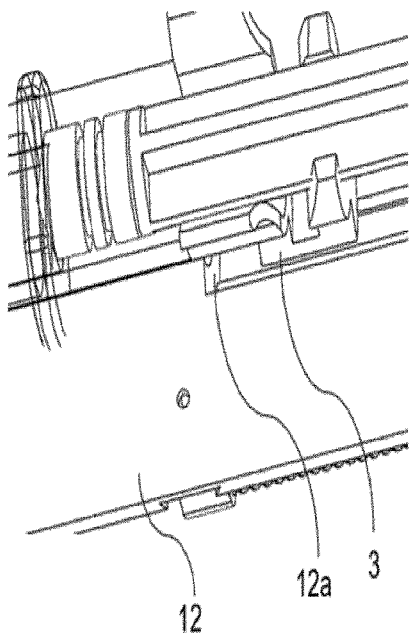

The resilient member (7) as shown in FIG. 8A, is arranged to facilitate the coupling mechanism as described above. The resilient member (7) may be a coiled spring as shown in FIG. 8A, or may be a band spring, constant force spring, ribbon or resilient wire; and is arranged between the housing base (12) and the connecting portion (34) of the container carrier unit (3). The resilient member (7) is configured to pull and move the container carrier unit (3) in the proximal direction, until the resilient member reaches a retracting relax configuration, so that said configuration of the resilient member (7) acts as a proximal stop element of the housing base (12) for the container carrier unit (3); or until the container carrier unit (3) hits a hard stop (12a) arranged on the housing base (12) which is acting as the proximal stop element, as shown in FIG. 8B. Since the resilient member (7) is pulling and moving the container carrier unit (3) in the proximal direction, the distal end of the guide slot (35a) or, in another embodiment, the holding ledge (35b) will remain engaged with the plunger pusher (2) by the resilient element (7), so that the plunger pusher (2) and the container carrier unit (3) is connected and axially movable together in both distal or proximal direction. Once the container carrier unit (3) met the proximal stop element of the housing base (12) as described above or once the resilient member (7) is no longer moving the container carrier unit (3) in the proximal direction, the connection between the container carrier unit (3) and the plunger pusher (2) is released. After the connection is released, the plunger pusher (2) is able to move proximally in relation to the container carrier unit (3). The plunger pusher is able to also move distally in relation to the container carrier unit (3).

Figure 9A:
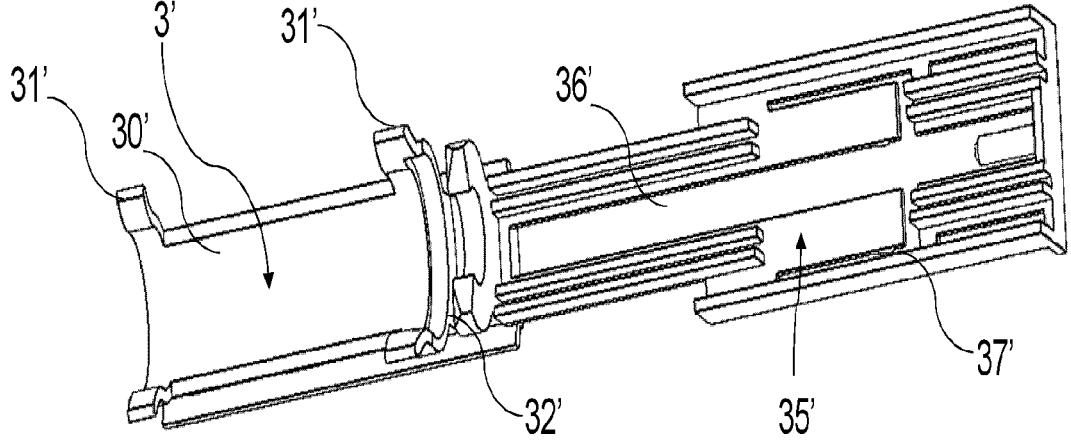
FIGS. 9A-9B displays another embodiment of the coupling element.
Figure 9B:
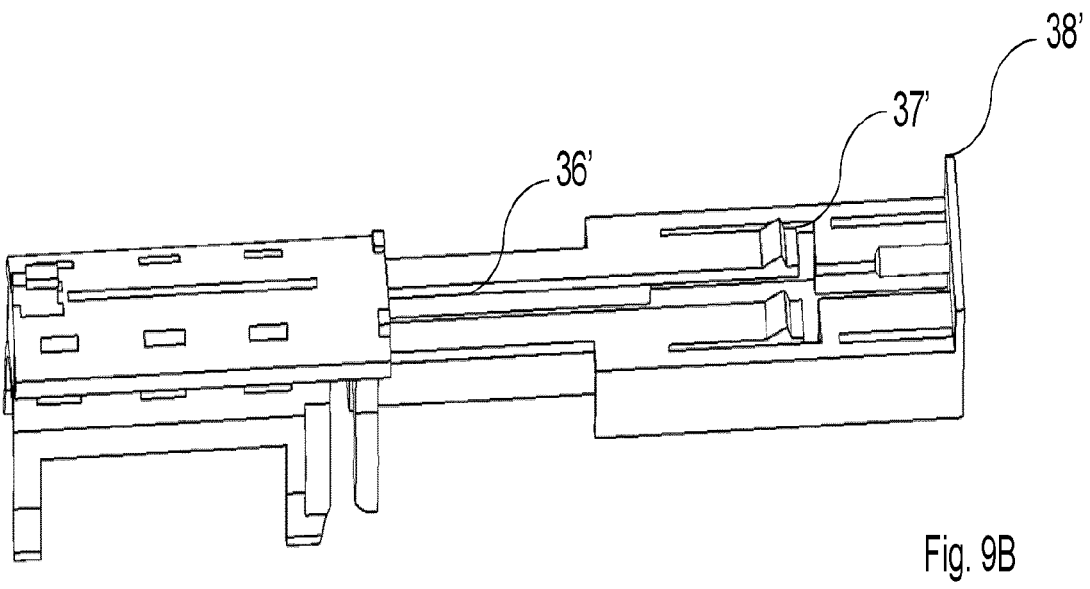

FIGS. 9A-9B illustrate the coupling mechanism in the second embodiment. The container carrier unit (3') in this embodiment is fixedly connected to a coupling element (35'). The coupling element (35') comprises a guide (36') configured to allow the pushing portion (21') of the plunger pusher (2') to pass through and move along the guide (36'). The coupling element (35') further comprises a distal ledge (38'), and a flexible member (37') having a fixed end and a free end which is radially movable in relation to the coupling element (35'). The flexible member (37') comprises a radially projecting ledge arranged on the free end, and wherein the ledge comprises a wedge surface arranged on its proximal surface and an abutting surface arranged on its distal surface.

Figure 10:
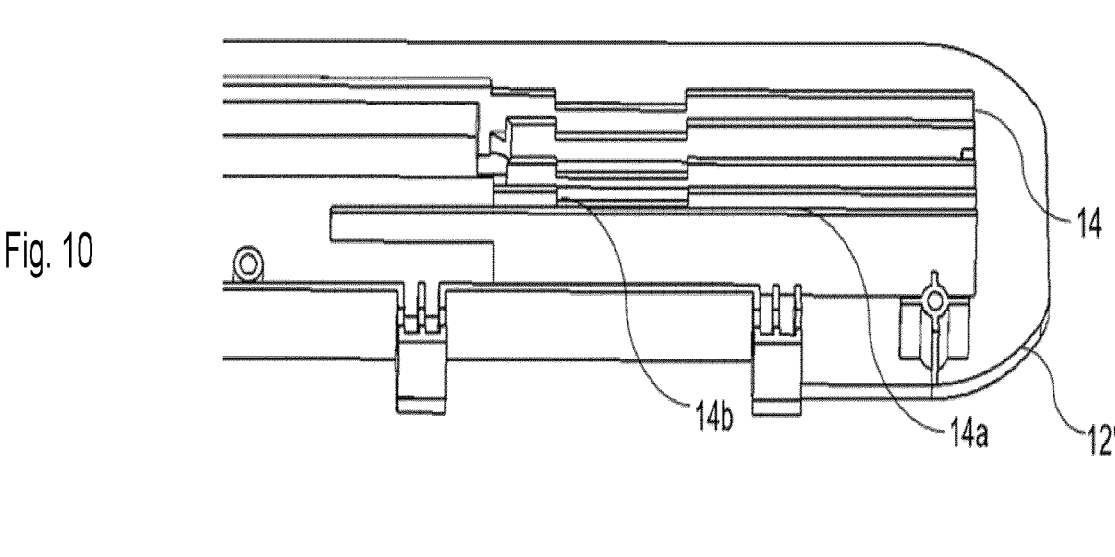
FIG. 10 displays the track on the housing for the coupling element in FIG. 7*a*-7*b*.

The housing base (12') in this embodiment comprises a track (14') as shown in FIG. 10. The track (14') comprises a support surface (14'a) which is configured to support the free end of the flexible member (37') of the coupling element (35'), so that the radially inward movement of the flexible member (37') is prevented. The track (14') further comprises a recess (14'b), configured to receive free end of the flexible member (37), so that once the free end of the flexible member (37') is aligned with the recess (14'b), the radially inward movement of the flexible member (37') is allowed. The recess (14'b) is defined as the proximal stop element of the housing base (12) for the container carrier unit (3') or arranged corresponding to the hard stop of the housing base (12') being met by the container carrier unit (3').

Figure 11:
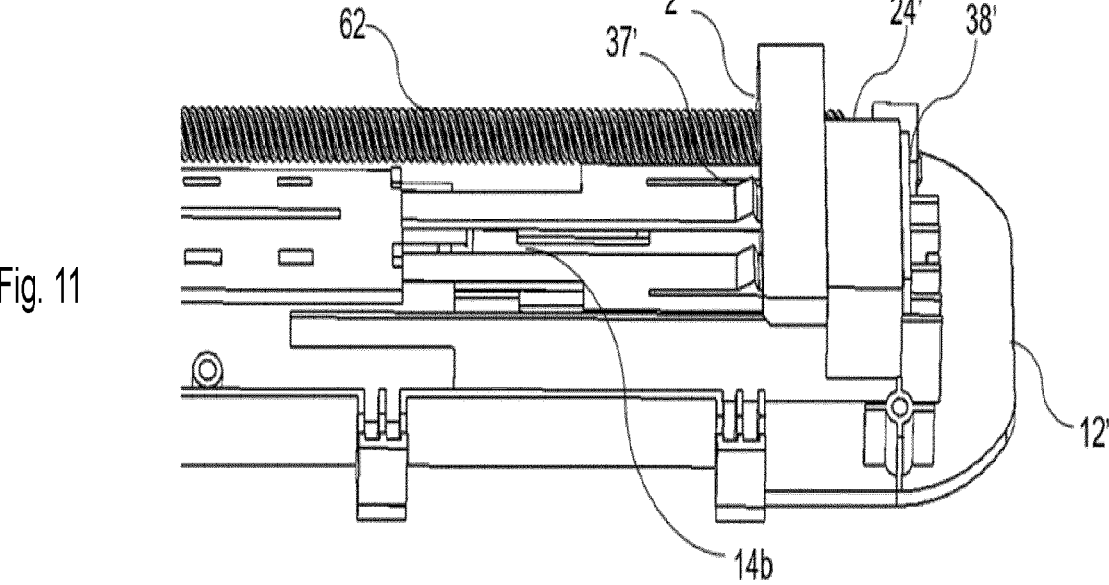
FIG. 11 displays the coupling element in FIG. 7*a*-7*b* and the track on the housing arranged in the power pack assembly.

As shown in FIG. 11, the abutting surface of the ledge of the flexible member (37') is configured to abut the plunger pusher (2'). When the free end of the flexible member (37') is supported by the support surface (14'a), the plunger pusher (2') is connected to the container carrier unit (3') through the abutment formed between the flexible member (37') and the plunger pusher (2'); so that the plunger pusher (2'), the container carrier unit (3'), and the coupling element (35') are all connected together and proximally movable together. The plunger pusher (2'), preferably comprises an extension piece (24') positioned between the ledge of the flexible member (37') and the distal ledge (38') of the coupling element (35'); so that the plunger pusher (2') and the container carrier unit (3') are connected and movable together in the distal direction. The extension piece (24') is an optional feature for connecting the plunger pusher (2') to the distal ledge (38'), which can be replaced by connecting the plunger pusher (2') directly to the distal ledge (38').

Once the plunger pusher (2') moves the container carrier unit (3') and the coupling element (35') in the proximal direction, and the proximal stop of the housing base (12) is met, meaning the free end of the flexible arm (37') of the coupling element (35') is now aligned with the recess (14'b), the free end of the flexible arm (37') will flex radially inward under the biasing from the plunger pusher (2'). Once the free end of the flexible arm (37') is received in the recess (14'*b*), the plunger pusher (2') can pass the abutting surface of the flexible arm (37') and disengage with the coupling element (35') and the container carrier unit (3'), so that the plunger pusher (2') is axially movable in relation to the container carrier unit (3'). In a preferred embodiment, the extension piece (24') is configured to move in the proximal direction together with the plunger pusher (2') until the free end of the flexible arm (37') will flex radially inward under the biasing from the plunger pusher (2'). The extension piece (24') is then configured to press on the flexible arm (37'), so that the flexible arm (37') will not flex back after the plunger pusher (2') has disengaged with the flexible arm (37'), affixing the coupling element (35') and the container carrier unit (3') to the housing base (12').

The resilient member (7) as described above in the first embodiment, may also be used in the second embodiment, since the resilient member is not only arranged for facilitating the coupling mechanism, but can be used for performing the actuation of the proximal movement of the container carrier unit (3; 3'). Such as, if the power pack assembly is used in a reusable medicament delivery device, which is an injection device, the resilient member (7) can be used to perform an auto penetration operation. In this embodiment, the plunger pusher (2; 2') is configured to regulate an exerted force of the resilient member (7) on the container carrier unit (3; 3').

Figure 12:
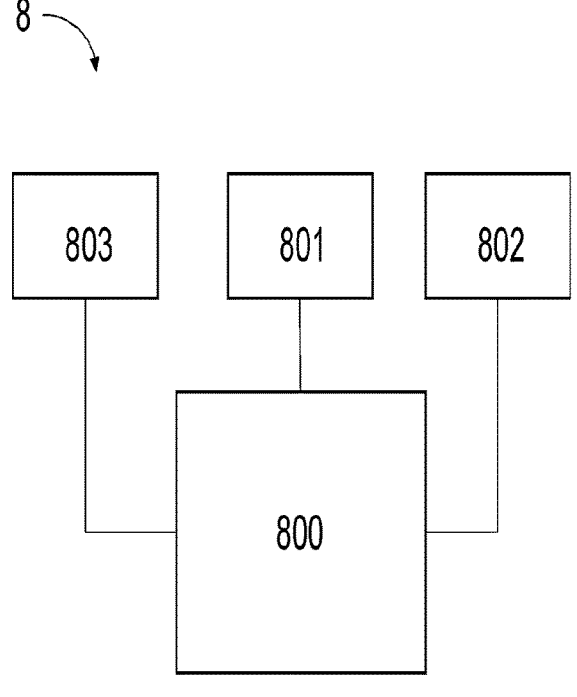
FIGS. 12-13 displays the connection between the electronics set and the motor and the flow chart of the control sequence of the controller.
Figure 13:
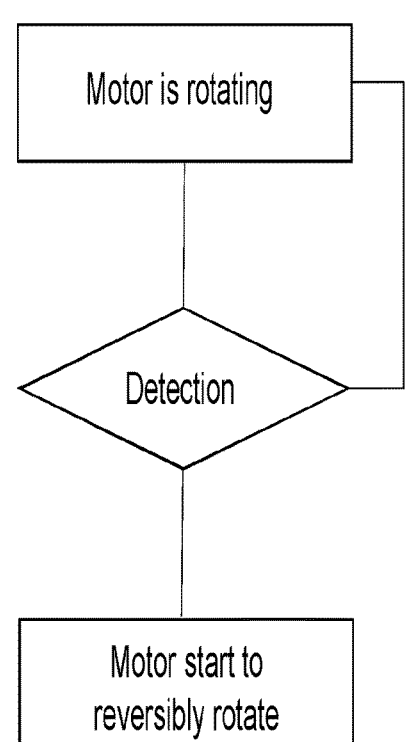

The power pack assembly further comprises an electronics set (8) as shown in FIG. 12-13, which comprises a primary detector (801) and a controller (800) configured to control the motor (803). The controller (800), preferably a micro processing unit (MPU) or a micro controlling unit (MCU) or another other suitable processor, has been programmed with a stop condition, which is triggered by a change of input from the primary detector (801). As shown in FIG. 13, the power pack assembly is started with the rotation of the rotation motor (803), and once there is the change of input from the primary detector (801), the controller (800) will adjust the control the rotary motor (803), so that the rotary motor (803) will start to reversibly rotate, namely rotate in an opposite direction.

The primary detector (801) is configured to detect a position of the plunger pusher (2; 2') in relation to the housing base (12; 12'); or a contact of the plunger pusher (2; 2') with a portion of the housing base (12). Such position or contact is acted as a stop event and defined as a distal virtual stop for the container carrier unit (3; 3') and the plunger pusher (2; 2'). The primary detector (801) can be an optical sensor or an infra-red emitter and receiver, so that, once the plunger pusher (2; 2') crosses the light beam, it will be detected by the primary detector (801); or it can be a magnetic encoder, capacitance sensor, a impedance sensor, a mechanical switch, a pressure sensor, a force resistor or any other suitable sensor using for detecting the position of an object or a contact of an object.

Since the lead screw (62) is configured to transmit the output force of the motor (803) to the plunger pusher (2; 2'), the proximal or distal movement of the plunger pusher (2; 2') is determined by the rotation or reverse rotation of the rotation motor (803).

When the power pack assembly is used in the medicament delivery device (100), the medicament delivery device (100) comprises a protective cap configured to cover a medicament delivery member and required the user of the medicament delivery device (100) removed the protective cover before initiating an operation of the medicament delivery sequence. The operation of the power pack assembly is therefore preferred to start with a distal movement of the plunger pusher (2; 2') together with the container carrier unit (3; 3'). The distal movement of the container carrier unit (3; 3') causes the medicament container (4) to move in the distal direction with the medicament delivery member, so that the medicament delivery member is configured to detach from the protective cap and the protective cap will therefore detach from the medicament delivery device (100); which provides an indication to the user that the medicament delivery device (100) is ready. Such distal movement may also be used to reset the power pack assembly, such like tensioning the resilient member (7) or, when the power pack assembly is associated with the reusable medicament delivery device (100), to adjust the exposure of the medicament delivery member, like hiding the medicament delivery member at the beginning and exposing the medicament delivery member during the operation of the medicament delivery sequence.

Once the virtual distal stop is met, the primary detector (801) detects the stop event, the primary detector (801) passes a change input to the controller (800) and the controller (800) controls the rotary motor (803) start to reversibly rotate. The reverse rotation of the rotary motor (803) causes the reverse rotation of the lead screw (62), so the plunger pusher (2; 2') start to move in the proximal direction.

When the plunger pusher (2; 2') and the container carrier unit (3; 3') are connected through one of the coupling mechanisms described above, the plunger pusher (2; 2') is configured to move the container carrier unit (3; 3') in the proximal direction, such as a penetration mechanism when the power pack assembly is used in an injection device or an exposure of a spray nozzle when the power pack assembly is used in an inhalation device.

Once the container carrier unit (3; 3') interacts with the proximal stop element on the housing base (12; 12'), the plunger pusher (2; 2') is released from the container carrier unit (3; 3'); and the plunger pusher (2; 2') continues to move proximally a further distance for performing the medicament delivery operation.

While the power pack assembly is used in the reusable medicament delivery device (100), there may further be a secondary detector (802) arranged in the reusable medicament delivery device (100) configured to detect a condition of the reusable medicament delivery device (100); such as the position of a protective cap of the reusable medicament delivery device (100), or a position of another protective cap of the medicament container of the reusable medicament delivery device (100) or an exposure or a position of a medicament delivery member. The secondary detector (802) is connected to the controller (800) of the power pack assembly.

The secondary detector (802) can be the same or different type of sensor as the primary detector and connected to the controller (800). The stop condition may be defined as a change of input from the secondary detector (802). For example, this embodiment may be used in combination of the reusable medicament delivery device (100) with an auto protecting cap removal mechanism, so that the power pack assembly is used to pull the medicament container (4) distally until the protecting cap of the reusable medicament delivery device (100) is detached by hitting on a blocking element on either the housing (100) of the reusable medicament delivery device (100) or the housing base (12; 12') of the power pack assembly. The distal movement of the plunger pusher (2; 2') and the container carrier unit (3; 3')

will sequentially turn into the proximal movement and prepare to start the medicament delivery operation.

The inventive concept has been described above with reference to a few examples. However, as is readily appreciated by a person skilled in the art, other embodiments than the ones disclosed above are equally possible within the scope of the inventive concept, as defined by the appended claims.

The invention claimed is:

1. A power pack assembly for a medicament delivery device comprising:

a housing base extending along a longitudinal axis (L) and having a proximal end near a dose delivery site and a distal end opposite the proximal end;

a container carrier unit arranged longitudinally and bi-directionally movable in relation to the housing base;

a plunger pusher releasably connected to the container carrier unit;

a resilient member arranged on the proximal end between the housing base and the container carrier unit, the resilient member being configured to exert a pulling force on the container carrier unit towards the proximal end; and an actuator unit connected to the plunger pusher, wherein the actuator unit is configured to drive the plunger pusher in a sequence in which the plunger pusher and the container carrier unit move together distally in relation to the housing base followed by a proximal movement, provided by the resilient member, until the container carrier unit interacts with a proximal stop element of the housing base whereby the plunger pusher is released from the container carrier unit, and the plunger pusher continues to move proximally a further predetermined distance.

2. The power pack assembly according to claim 1, wherein the plunger pusher is releasably connected to the container carrier unit by a coupling element, and wherein the coupling element is fixedly or integrally connected to the container carrier unit.

3. The power pack assembly according to claim 2, wherein the coupling element comprises a flexible member.

4. The power pack assembly according to claim 3, wherein the housing base comprises a track which is configured to force the flexible member to be in contact with the plunger pusher until the container carrier unit interacts with the proximal stop element of the housing base such that the flexible member is allowed to flex and thereby release the plunger pusher from the container carrier unit.

5. The power pack assembly according to claim 3, wherein the flexible member comprises a ledge which contacts with the plunger pusher.

6. The power pack assembly according to claim 1, wherein the actuator unit is configured to regulate the exerted force of the resilient member on the container carrier unit.

7. The power pack assembly according to claim 1, wherein the actuator unit comprises a driving force element and a lead screw, wherein a first end of the lead screw is connected to the driving force element through a gearbox, and wherein a second end of the lead screw is connected to the plunger pusher.

8. The power pack assembly according to claim 7, wherein the driving force element is a motor.

9. The power pack assembly according to claim 8, wherein the power pack assembly further comprises an electronics set, which comprises a controller configured to control the motor.

10. The power pack assembly according to claim 9, wherein drive the plunger pusher and the container carrier unit are together distally moved in relation to the housing base until a distal stop is met, and wherein the distal stop is a programmable stop condition in the controller such that the distal movement of the plunger pusher and the container carrier unit is stopped when the stop condition has occurred.

11. The power pack assembly according to claim 1, wherein the plunger pusher further comprises a rod element.

12. The power pack assembly according to claim 1, wherein the medicament delivery device further comprises a secondary sensor configured to detect an event of the medicament delivery device, and wherein the event is the stop condition of the controller.

13. The power pack assembly according to claim 1, wherein the resilient member may comprise of a band spring, constant force spring, ribbon, or resilient wire.

14. A power pack assembly for a medicament delivery device comprising:

a housing extending along a longitudinal axis (L) and having a proximal end near a dose delivery site, a distal end opposite the proximal end, and a track;

a container carrier unit arranged longitudinally and bi-directionally movable relative to the housing;

a plunger pusher comprising a transition portion, where the plunger pusher is releasably connected to the container carrier unit;

a resilient member arranged on the proximal end between the housing and the container carrier unit, the resilient member being configured to exert a pulling force on the container carrier unit towards the proximal end; and an actuator unit operatively connected to the transition portion, wherein the actuator unit moves the plunger pusher axially such that the container carrier unit moves axially distally relative to the housing followed by proximal movement, provided by the resilient member, of the plunger pusher and the container carrier unit until the container carrier unit contacts a proximal stop on the housing whereby the plunger pusher disengages from the container carrier unit and continues to move proximally a further predetermined distance.

15. The power pack assembly of claim 14, wherein the actuator unit comprises a lead rod operatively engaged with the transition portion.

16. The power pack assembly of claim 15, wherein the lead rod comprises screw threads and rotates relative to the plunger pusher and is axially fixed to the housing.

17. The power pack assembly of claim 15, wherein a releasable connection between the container carrier unit and the plunger pusher is a coupling element comprising a flexible member.

18. The power pack assembly of claim 15, wherein the lead rod is moved by a motor axially fixed relative to the housing.

19. The power pack assembly of claim 15, wherein the plunger pusher further comprises a pushing portion that engages with and axially moves a plunger rod relative to a medicament container positioned in the container carrier unit when the lead rod is rotated and the plunger pusher disengages from the container carrier unit.

20. The power pack assembly of claim 14, wherein the actuator unit is configured to regulate the exerted force of the resilient member on the container carrier unit.

* * * * *